(12) United States Patent
Kirenko

(10) Patent No.: US 10,292,662 B2
(45) Date of Patent: May 21, 2019

(54) DEVICE AND METHOD FOR OBTAINING PULSE TRANSIT TIME AND/OR PULSE WAVE VELOCITY INFORMATION OF A SUBJECT

(71) Applicant: KONINKLIJKE PHILIPS N.V., Eindhoven (NL)

(72) Inventor: Ihor Olehovych Kirenko, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 87 days.

(21) Appl. No.: 15/039,135

(22) PCT Filed: Nov. 19, 2014

(86) PCT No.: PCT/EP2014/074950
§ 371 (c)(1),
(2) Date: May 25, 2016

(87) PCT Pub. No.: WO2015/078735
PCT Pub. Date: Jun. 4, 2015

(65) Prior Publication Data
US 2017/0164904 A1    Jun. 15, 2017

Related U.S. Application Data

(63) Continuation of application No. PCT/EP2014/074950, filed on Nov. 19, 2014.

(30) Foreign Application Priority Data

Nov. 27, 2013 (EP) ..................................... 13194603

(51) Int. Cl.
*A61B 5/00* (2006.01)
*A61B 5/021* (2006.01)
(Continued)

(52) U.S. Cl.
CPC .......... *A61B 5/7278* (2013.01); *A61B 5/0205* (2013.01); *A61B 5/02125* (2013.01);
(Continued)

(58) Field of Classification Search
CPC . G06T 7/0012; G06T 7/11; G06T 7/20; G06T 2207/30104; A61B 5/7278;
(Continued)

(56) References Cited

U.S. PATENT DOCUMENTS 9,451,905 B2    9/2016 Op Den Buijs
2010/0195473 A1    8/2010 Tsuyama
(Continued)

FOREIGN PATENT DOCUMENTS

DE    19741982    10/1998
EP    2000084    12/2008
(Continued)

OTHER PUBLICATIONS

Verkruysse et al., "Remote plethysmographic imaging using ambient light", Optics Express, 16(26), Dec. 22, 2008, pp. 21434-21445.
(Continued)

*Primary Examiner* — Rex R Holmes

(57) ABSTRACT

The present invention relates to a device and method for obtaining pulse transit time and/or pulse wave velocity information of a subject (14). Based on a set of image frames (19) of a subject (14) and detected motion of body parts of the subject (14) regions of interest are selected from different non-moving body parts and pulse transit time and/or pulse wave velocity information is obtained from acquired PPG signals extracted from different regions of interest and the respective determined physical distance between the respective regions of interest.

20 Claims, 5 Drawing Sheets

(51) Int. Cl.
| | |
|---|---|
| *A61B 5/024* | (2006.01) |
| *A61B 5/11* | (2006.01) |
| *G06T 7/254* | (2017.01) |
| *G06T 7/11* | (2017.01) |
| *A61B 5/0205* | (2006.01) |
| *G06T 7/00* | (2017.01) |
| *G06T 7/20* | (2017.01) |
| *A61B 5/08* | (2006.01) |
| *A61B 5/091* | (2006.01) |
| *A61B 5/1455* | (2006.01) |

(52) U.S. Cl.
CPC ........ *A61B 5/02416* (2013.01); *A61B 5/1128* (2013.01); *A61B 5/7214* (2013.01); *G06T 7/0012* (2013.01); *G06T 7/11* (2017.01); *G06T 7/20* (2013.01); *G06T 7/254* (2017.01); *A61B 5/0077* (2013.01); *A61B 5/02427* (2013.01); *A61B 5/0816* (2013.01); *A61B 5/091* (2013.01); *A61B 5/14552* (2013.01); *A61B 2576/00* (2013.01); *G06T 2207/10016* (2013.01); *G06T 2207/30076* (2013.01); *G06T 2207/30104* (2013.01)

(58) Field of Classification Search
CPC . A61B 5/7214; A61B 5/0205; A61B 5/02125; A61B 5/02427; A61B 5/0077; A61B 2576/00; A61B 5/14552; A61B 5/1128; A61B 5/091
See application file for complete search history.

(56) References Cited

U.S. PATENT DOCUMENTS

| | | |
|---|---|---|
| 2013/0018272 A1 | 1/2013 | Hori |
| 2013/0046192 A1* | 2/2013 | Lin ............... A61B 5/02007 600/500 |

FOREIGN PATENT DOCUMENTS

| | | | |
|---|---|---|---|
| EP | 2631874 | 8/2013 | |
| EP | 2631874 A1 * | 8/2013 | ......... A61B 5/02125 |
| JP | 2004321253 | 11/2004 | |
| JP | 2013043017 | 3/2013 | |
| WO | 2010/004940 | 1/2010 | |
| WO | 2012007423 | 1/2012 | |
| WO | 2012/093320 | 7/2012 | |
| WO | 2012/140531 | 10/2012 | |
| WO | 2013030745 | 3/2013 | |
| WO | 2013/0166341 | 11/2013 | |

OTHER PUBLICATIONS

Lempe, et al., "ROI selection for Remote Photoplethysmography", 2013.
Wieringa, et al., "Contactless Multiple Wavelength Photoplethysmographic Imaging: A First Step Toward "SpO2 Camera" Technology," Ann. Biomed. Eng. 33, 1034-1041 (2005).
Addison et.al. J., "Developing an algorithm for pulse oximetry derived respiratory rate (RRoxi): a healthy volunteer study", Journal of Clinical Monitoring and Computation, 26:45-51 (2012).
L. Panini, R. Cucchiara, "A Machine learning approach for human posture detection in domotics applications", Proceedings of the 12th International Conference on Image analysis and Processing (ICIAP'2003).
Humberto Souto Junior, Soraia Raupp Musse, "Automatic Detection of 2D Human Posture based on Single Images", Proceedings of Graphics, Patters and Images (Sibgraphi), 2011, Aug. 2011.
U. Rubins, et al., "Real-time Photoplethysmography Imaging System,,", IFMBE proceedings 34, pp. 183-186, 2011.
Nilsson, et al., "Respiratory variations in the photoplethysmographic waveform: acute hypovolaemia during spontaneous breathing is not detected", 2010 Physiol. Meas. vol. 31, No. 7.
Nilsson, et al., "Respiratory variations in the reflection mode photoplethysmographic signal. Relationships to peripheral venous pressure", Medical and Biological Engineering and Computing May 2003; 41(3):249-54.
Sola, et al., "Ambulatory monitoring of the cardiovascular system: the role of Pulse Wave Velocity", in New Developments in Biomedical Engineering, I-Tech Education and Publishing, Vienna, Austria, ISBN 978-953-7619-57-1.
Kwon, et al., "Validation of heart rate extraction using video imaging on a built-in camera system of a smartphone", 2012.
Allen, "Photoplethysmography and its application in clinical physiological measurement", Physiol. Meas. 28 (2007) R1-R39.
Blacher, et al., "Large-artery stiffness, hypertension and cardiovascular risk in older patients", Clinical Practice Cardiovascular Medicine Sep. 2005 vol. 2 No. 9.
Myllyla, et al., "Human Heart Pulse Wave Responses Measured Simultaneously at Several Sensor Placements by TwoMR-Compatible Fibre Optic Methods", Hindawi Publishing Corporation, Journal of Sensors, vol. 2012, Article ID 769613, 8 pages.

* cited by examiner

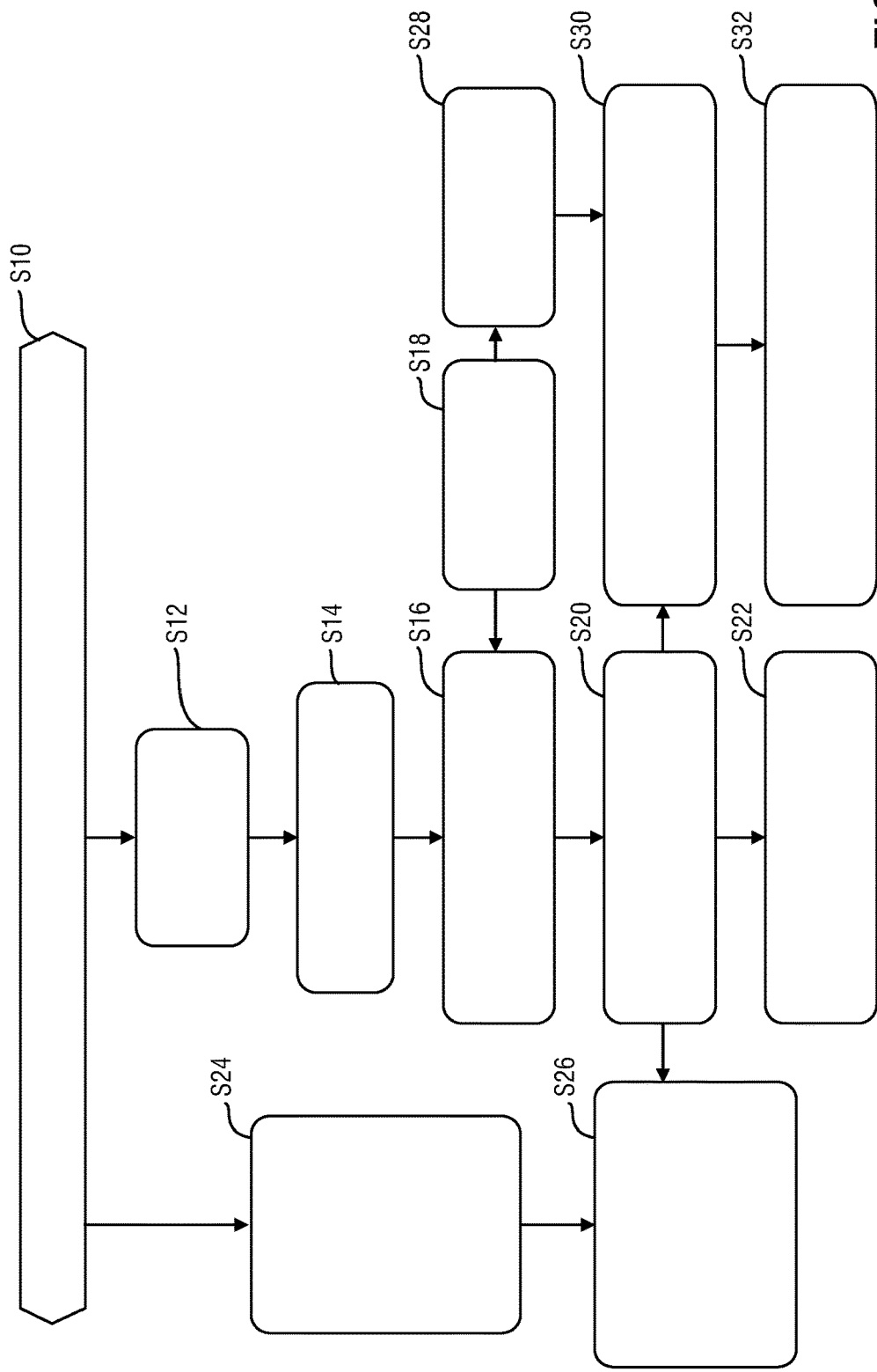

DEVICE AND METHOD FOR OBTAINING PULSE TRANSIT TIME AND/OR PULSE WAVE VELOCITY INFORMATION OF A SUBJECT

CROSS REFERENCE TO RELATED APPLICATIONS

This application is the U.S. National Phase application under 35 U.S.C. § 371 of International Application No. PCT/EP2014/074950, filed Nov. 19, 2014, published as WO 2015/078735 on Jun. 4, 2015, which claims the benefit of European Patent Application Number 13194603.0 filed Nov. 27, 2013. These applications are hereby incorporated by reference herein.

FIELD OF THE INVENTION

The present invention relates to a device and a method for obtaining pulse transit time and/or pulse wave velocity information of a subject, such as a person or animal.

BACKGROUND OF THE INVENTION

Currently, as leading cause of mortality in western countries cardiovascular diseases (CVD) are largely responsible for the ever increasing costs of healthcare systems.

Research studies on hypertension have, so far, generally focused on vascular resistance and small arteries. The high prevalence of systolic hypertension in patients older than 50 years and the development of noninvasive Doppler and echo tracking techniques have made it possible to determine large-artery stiffness with a high degree of reproducibility. Increased arterial stiffness and disturbed wave reflections are the basis for understanding reduced aortic elasticity and systolic hypertension, particularly in older people. This hemodynamic pattern results from mechanical factors and other pressure-independent risk factors, such as diabetes mellitus, renal failure, obesity and severe atherosclerosis.

The roles of arterial stiffness and wave reflections in hypertension have been elucidated by modern interpretations of the blood-pressure curve in relation to its propagation, mechanisms of systolic-blood-pressure amplification, and the pulse-pressure amplitude. New predictors of cardiovascular risk have been identified, such as increased pulse pressure and pulse-wave velocity as well as disturbed wave reflections, all of which are independent predictors of cardiovascular risk that are more powerful than either systolic or diastolic blood pressure alone. Therapeutic trials are investigating ways to reduce stiffness, and thereby allow the selective reduction of systolic and pulse pressure in hypertensive patients with or without advanced renal failure.

Because several studies have recently highlighted the important role that arterial stiffness plays in the development of CVD, and since central stiffness has been shown to be the best independent predictor of both cardiovascular and all-cause mortality, stiffness might be considered to be the missing vascular-related parameter in ambulatory cardiovascular monitoring. However, the only available technique for measuring arterial stiffness non-invasively so far is the so-called pulse wave velocity (PWV).

EP 2 000 084 A1 discloses an apparatus for obtaining pulse wave velocity information including a light-emitting unit, an image sensor configured to capture images, in time sequence, relating to a living body, a lens, an extreme-occurrence-time obtaining unit configured to obtain times T1 and T2 at which extremes occur in time sequence with respect to brightness values of a first region and a second region of each of the captured images, the time T1 being obtained for one of the first regions and the time T2 being obtained for one of the second regions, and a PWV calculation unit configured to calculate a pulse wave velocity according to expression $P=(Y L/f)/(T2-T1)$, where Y represents a distance on the image sensor, the distance corresponding to a distance between the first region and the second region, f represents the focal length of the lens, and L represents a distance between the lens and the living body.

EP 2 631 874 A1 discloses a system and method for determining an arterial pulse transit time of a subject of interest in a remote sensing environment. A video imaging system is used to capture a time varying source images of a proximal and distal region of a subject intended to be analyzed for arterial pulse transit time. A time series signal for each of the proximal and distal regions is extracted from the source images and a phase of each of the extracted time series signals is computed. A difference is then computed between these phases. This phase difference is a monotonic function of frequencies in the signals. From the monotonic function, an arterial pulse transit time of the subject is extracted. The subject's arterial pulse transit time is then communicated to a computer system. The computer system determines blood pressure, blood vessel blockage, blood flow velocity, or a peripheral neuropathy.

US 2010/0195473, WO 2012/093320 A2 and the article of W. Verkruijsse et al.: "A novel biometric signature: multi-site, remote (>100 m) photo-plethysmography using ambient light", Technical Note PR-TN 2010/00097, March 2010, disclose further developments of the applicant regarding a device and method for remote photo-plethysmography.

WO 2013/1663341 A1 discloses physiological characteristic detection based on reflected components of light.

DE 197 41 982 discloses a system for local non-invasive functional indicating of dermal blood perfusion.

US 2013/0046192 A1 discloses an image-based PWV measurement device and method.

SUMMARY OF THE INVENTION

It is an object of the present invention to provide a device and a method for unobtrusively, reliably and efficiently obtaining pulse transit time and/or pulse wave velocity information of a subject that enable a fast but reliable determination and/or monitoring of the subject's health condition and a better prediction of the subject's health status deteriorations.

In a first aspect of the present invention a device for obtaining pulse transit time and/or pulse wave velocity information of a subject is presented, said device comprising an interface for receiving a set of image frames of a subject acquired by an imaging unit, a motion detection unit for detecting motion of different body parts of the subject, an ROI selection unit for selecting at least two regions of interest at body parts of the subject within said set of image frames, a signal extraction unit for extracting at least two photoplethysmographic, PPG, signals from at least two selected region of interest from said set of image frames, a motion correction unit for controlling said ROI selection unit to select only regions of interest at substantially unmoved body parts and/or for controlling said signal extraction unit to extract a PPG signal only from regions of interest at substantially unmoved body parts or to correct PPG signals extracted from regions of interest at moving body parts, a distance determination unit for determining the physical distance between selected regions of interest within an image frame, and a calculation unit for determining pulse transit time and/or pulse wave velocity information from the PPG signals extracted from different regions of interest and the respective determined physical distance between the respective regions of interest.

In a second aspect of the present invention a corresponding method of obtaining pulse transit time and/or pulse wave velocity information of a subject is presented.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method and computer program have similar and/or identical preferred embodiments as the claimed device and as defined in the dependent claims.

The present invention provides a reliable and efficient device and method that provide PWV measurement automatically, continuously, and in a non-obtrusive way, while remaining unaffected by movements of the subject's body or body portions or changes in body position or being automatically adjusted to body pose. Further, it enables a continuous measurement of transit time of a pressure pulse when travelling through the body, e.g. when travelling from the Aortic Valve to the Strenum (the so-called av2sPTT). Further, pulse transit time (PTT) can be determined and PWV values can be calculated, e.g. in the following way:

$$PWV=D/PTT,$$

where D is the length of an arterial segment and the pulse transit time is defined as:

$$PTT=PATd-PATp,$$

where PATp is the arrival time of the pressure pulse at the point closer to the heart and PATd is the arrival time of the pressure pulse at extremity.

Thus, the present invention substantially provides a signal processing chain to acquire PTT and/or PWV information from image data by combing an automatic detection of several non-moving ROIs on skin, determination (e.g. estimation) of the physical distance between those ROI, calculation of phase shift between those PPG signals. Contrary to known systems using several contact PPG sensors placed on body parts (e.g. legs, arms, forehead), synchronized with each other or/and with ECG, all the information used according to the present invention comes from one single optical sensor, namely an imaging unit such as a video camera.

EP 2000084 A1 discloses a specific hardware setup for transmissive or reflective PPG on a finger, but does not address the aspects of measurement of PWV on more than one part of a body, which is neither desired nor possible using the disclosed hardware setup. In contrast, the present invention discloses a multi-spot measurement of PPG signals and an analysis of changes in PPG morphology depending on motion on different body locations.

In a preferred embodiment said signal extraction unit is configured to select a plurality of regions of interest from a plurality of different body parts of the subject, wherein said signal extraction unit is configured to extract a plurality of PPG signals from said plurality of selected regions of interest and wherein said calculation unit is configured to determine pulse transit time and/or pulse wave velocity information from the PPG signals extracted from a plurality of different regions of interest and the respective determined physical distance between the respective regions of interest. By this multi-site PPG measurement, i.e. by obtaining multiple PPG signals from multiple ROIs from different body parts, the reliability and accuracy of the obtained pulse transit time and/or pulse wave velocity information of a subject can be increased.

In another embodiment said calculation unit is configured to determine a first body map indicating the determined pulse transit time and/or pulse wave velocity information for the respective body parts. This body map provides the caregiver with a good and quick overview of healthy and potentially unhealthy region of the subject's body.

Preferably, the device further comprises a vital signs determination unit for determining vital sign information from the PPG signals extracted from one or more selected regions of interest. Several vital signs of different physiological origin (e.g. PPG, breathing motion) may be acquired from multiple locations of the subject's body, simultaneously with context information (e.g. body motion, distance between ROIs). Signal processing methods are applied to extract derivative vital signs based on combined analysis of measured physiological signals and context information.

Vital signs of a person, for example the heart rate (FIR), the respiration rate (RR) or the blood oxygen saturation, serve as indicators of the current state of a person and can be used as predictors of medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heart beat. Photoplethysmography (PPG) is an optical measurement technique that evaluates a time-variant change of light reflectance or transmission of an area or volume of interest. PPG is based on the principle that blood absorbs more light than surrounding tissue, so variations in blood volume with every heart beat affect transmission or reflectance correspondingly. Besides information about the heart rate, a PPG waveform (also referred to as PPG signal) can comprise information attributable to further physiological phenomena such as the respiration. By evaluating the transmissivity and/or reflectivity at different wavelengths (typically red and infrared), the blood oxygen saturation can be determined. Conventional pulse oximeters are often attached to the skin of the subject. Therefore, they are referred to as 'contact' PPG devices.

Recently, non-contact, remote PPG (RPPG) devices for unobtrusive measurements have been introduced. Remote PPG utilizes light sources or, in general radiation sources, disposed remotely from the subject of interest. Similarly, also a detector, e.g. a camera or a photo detector, can be disposed remotely from the subject of interest. Therefore, remote PPG systems and devices are considered unobtrusive and well suited for medical as well as non-medical everyday applications.

Verkruysse et al., "Remote plethysmographic imaging using ambient light", Optics Express, 16(26), 22 Dec. 2008, pp. 21434-21445 demonstrate that photoplethysmographic signals can be measured remotely using ambient light and a conventional consumer level video camera. One of the main advantages of camera-based vital signs monitoring over on-body sensors is the high ease-of-use: there is no need to attach a sensor, just aiming the camera at the skin/chest of the subject is sufficient. Another advantage of camera-based vital signs monitoring over on-body sensors is the potential for achieving motion robustness: cameras have a significant spatial resolution while contact sensors mostly consist of a single element detector.

Preferably, said vital signs determination unit is configured to determine the (changes of) arterial blood oxygen saturation at different body parts and determine a second body map indicating the determined arterial blood oxygen saturation for the respective body parts. A caregiver can thus easily see if the subject has any health problem, which is particularly useful in baby care and monitoring of premature and newborn babies.

In an advantageous embodiment the device further comprises a respiration determination unit for determining respiratory information, in particular respiration rate and/or changes of respiration volume, of the subject from said set of image frames at selected regions of interest. The respiration rate is one of the most important vital signs in healthcare which can be reliably obtained by the proposed device and method.

Further, in an embodiment said ROI selection unit is configured to select regions of interest from which the strongest and/or most reliable PPG signals can be extracted. For instance, regions of interest, from which the PPG signal showing the highest SNR, or regions of interest showing no or only a small amount of motion of the respective body part, may be selected. This increases the reliability and accuracy of the obtained information.

Advantageously, said calculation unit is configured to determine phase shifts between PPG signals extracted from different regions of interest and to determine pulse transit time and/or pulse wave velocity information from said phase shifts and the determined physical distance between the respective regions of interest. This provides a reliable way of determining pulse transit time and/or pulse wave velocity information.

Advantageously, said calculation unit is configured to determine differences in pulse shapes between PPG signals extracted from different regions of interest. This information may be used to facilitate the diagnosis and assessment of various vascular diseases, for instance lower limb peripheral arterial occlusion disease (PAOD).

In still another embodiment the device further comprises a body posture detection unit for detecting the body posture of the subject, wherein said calculation unit is configured to take the body posture into account in the determination of the pulse transit time and/or pulse wave velocity information. The body posture can be quite easily determined from image data of the subject, e.g. by pattern recognition or image detection algorithms. Knowing the body posture during the determination of the pulse transit time and/or pulse wave velocity information and/or characteristics of pulse signals this determination becomes reproducible and the information obtained at different times becomes comparable.

Preferably, said calculation unit is configured to monitor said pulse transit time and/or pulse wave velocity information over time. Hence, a subject, e.g. a patient in a hospital or a premature baby, can be safely and unobtrusively monitored all the time so that any critical change of the subject's health status can be quickly and reliably detected so that an alarm can be issued immediately.

In still another embodiment said calculation unit is configured to determine changes in blood pressure from the determined pulse transit time and/or pulse wave velocity information. Thus, another piece of valuable information can be obtained indicating the subject's health state.

In yet another embodiment the device further comprises an imaging unit for acquiring image frames of the subject. The device may then correspond to a camera device including the above described elements for obtaining pulse transit time and/or pulse wave velocity information of a subject.

According to another aspect the present invention provides a device for obtaining physiological information of a subject, said device comprising an interface for receiving a set of image frames of a subject acquired by an imaging unit, a motion detection unit for detecting motion of different body parts of the subject, an ROI selection unit for selecting at least two regions of interest at body parts of the subject within said set of image frames, a signal extraction unit for extracting at least two photoplethysmographic, PPG, signals from at least two selected regions of interest from said set of image frames, a motion correction unit for controlling said ROI selection unit to select only regions of interest at substantially unmoved body parts and/or for controlling said signal extraction unit to extract a PPG signal only from regions of interest at substantially unmoved body parts or to correct PPG signals extracted from regions of interest at moving body parts, a calculation unit for determining physiological information of the subject including one or more of diagnosis of diabetes, evaluation of local blood microcirculation, analysis of changes of local blood perfusion by analyzing PPG signals acquired from different body parts of the subject.

According to this aspect information from the PPG signals extracted from different regions of interest is evaluated. For instance, diagnosis of diabetes can be performed by analyzing the difference in phase and shape of two PPG signals acquired from both feet or both legs. Further, the local blood microcirculation and local blood perfusion acquired from different body parts can be analyzed simultaneously. Thus, multiple PPG signals from various body parts may be used for other applications apart from PTT and PWV analysis. In another embodiment the above described calculation unit for determining PTT and/or PWV information may be configured further to obtain such additional physiological information (i.e. regarding diabetes, local blood microcirculation, changes of local blood perfusion).

BRIEF DESCRIPTION OF THE DRAWINGS

These and other aspects of the invention will be apparent from and elucidated with reference to the embodiment(s) described hereinafter. In the following drawings

FIG. 6 shows a flowchart of an embodiment of a method according to the present invention.

DETAILED DESCRIPTION OF THE INVENTION

Figure 1:
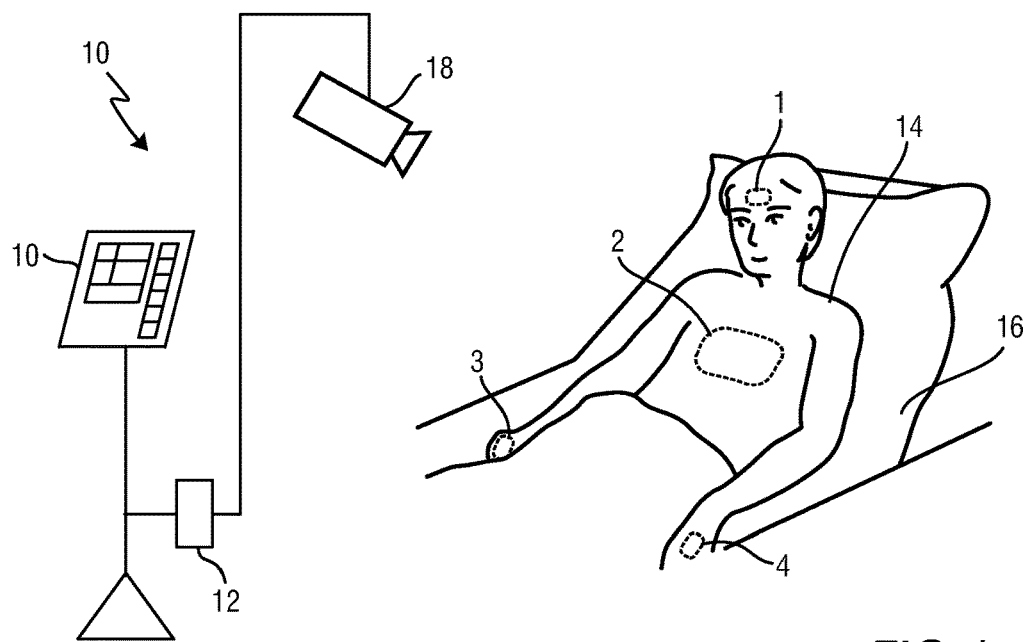
FIG. 1 shows an exemplary subject monitoring setup including an embodiment of a device according to the present invention.

FIG. 1 shows an exemplary embodiment of a monitoring system 10 including a device 12 for obtaining pulse transit time and/or pulse wave velocity information of a subject 14 according to the present invention. The subject 14, in this example a patient, lies in a bed 16, e.g. in a hospital or other healthcare facility. Image frames of the subject 14 are captured by means of a camera 18 including a suitable photosensor. The camera 18 forwards the recorded image frames to the device 12. The device 12 is further connected to an interface 20 for displaying the determined information and/or for providing medical personnel with an interface to change settings of the device 12, the camera 18 or the monitoring system 10. Such an interface 20 may comprise different displays, buttons, touchscreens, keyboards or other human machine interface means.

A monitoring system 10 as illustrated in FIG. 1 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, or the like. The uni- or bidirectional communication between the device 12, the camera 18 and the interface 20 may work via a wireless or wired communication interface. Other embodiments of the present invention may include a device 12, which is not provided standalone, but integrated into the camera 18 or the interface 20.

Figure 2:
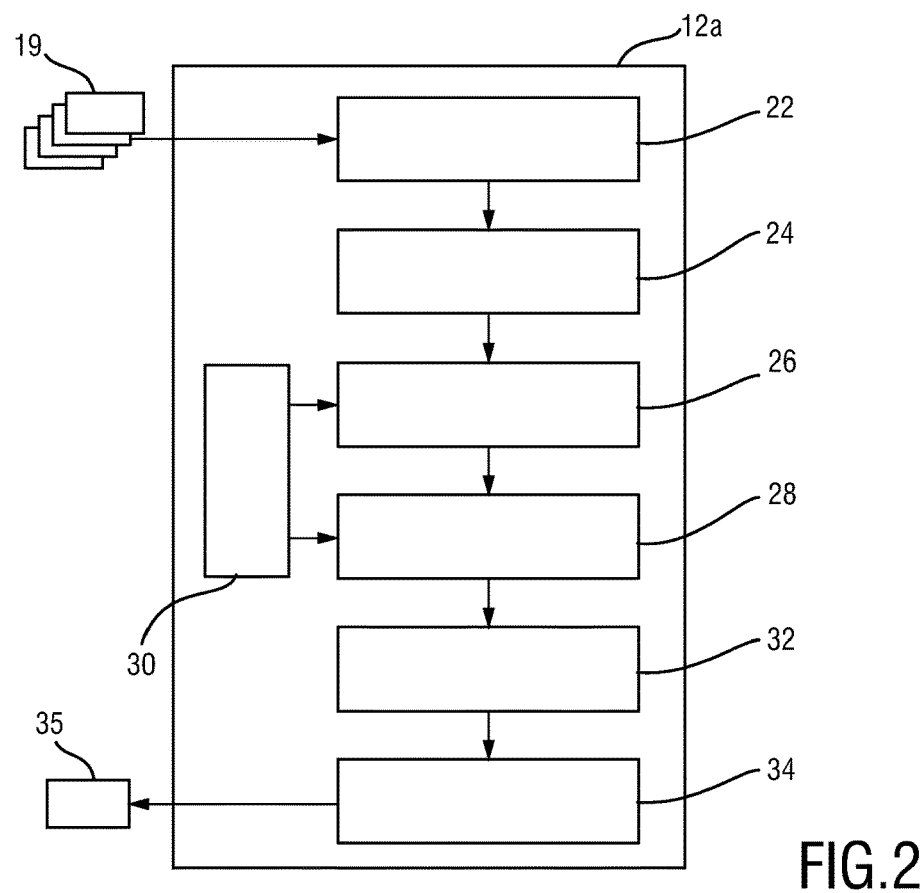
FIG. 2 shows a schematic illustration of a first embodiment of a device according to the present invention.

FIG. 2 shows a more detailed schematic illustration of a first embodiment 12a of the device 12 according to the present invention. The device 12a comprises an interface 22 for receiving a set of image frames of a subject. Thereby, the interface 22 may correspond to a wired or wireless network connection, any kind of serial connection or another standard or non-standard communication interface. The received image frames 19 may particularly correspond to a video sequence captured by means of an analog or digital photosensor, e.g. in a (digital) camera. Such a camera usually includes a photosensor, such as a CMOS or CCD sensor, which may also operate in a specific spectral range (visible, IR) or provide information for different spectral ranges. The camera may provide an analog or digital signal. The image frames 19 include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the subject. Thereby, an image pixel may correspond to one photosensitive element of a photodetector and its (analog or digital) output or may be determined based on a combination (binning) of a plurality of the photosensitive elements.

The device 12a further comprises a motion detection unit 24 for detecting motion of different body parts of the subject 14. Motion of a body part may be detected by comparing the current image with a reference image and simply counting the number of different pixels or by any other conventional motion detection algorithm.

The device 12a further comprises an ROI selection unit 26 for selecting at least two regions of interest at body parts of the subject 14 within said set of image frames 19. In FIG. 1 such different ROIs 1, 2, 3, 4 are schematically indicated. Selecting a region of interest may be made by detecting a skin area from which light is reflected that is received by the imaging unit. Advantageous methods for selecting a region of interest in order to derive PPG signals from the image frames obtained from the region of interest are generally known in the art, e.g. from Georg Lempe, Sebastian Zaunseder, Tm Wirthgen, et al. "ROI selection for Remote Photoplethysmography", Informatik aktuell, Bildverarbeitung für die Medizin, 2013.

The device 12a further comprises a signal extraction unit 28 for extracting at least two photoplethysmographic (PPG) signals from at least two selected regions of interest from said set of image frames 19. The extraction of PPG signals from an imaging unit is widely known in the art of vital signs monitoring and remote PPG. The principle is e.g. described in the above mentioned paper of Verkruysse et al. Such a signal extraction unit 26 may particularly correspond to an analog or digital signal processor. A PPG signal may particularly correspond to a signal representing fluctuations in the light intensity determined based on a time series of image frames 19. Such a PPG signal may be representative of a vital sign of a subject such as a heart rate, the respiratory rate or the (arterial) blood oxygen saturation. The signal extraction unit 26 may particularly extract the PPG signal based on multiple image pixels and/or based on a series of time-consecutive image frames.

The device 12a further comprises a motion correction unit 30 for controlling said ROI selection unit 26 to select only regions of interest at substantially unmoved body parts and/or for controlling said signal extraction unit 28 to extract a PPG signal only from regions of interest at substantially unmoved body parts or to correct PPG signals extracted from regions of interest at moving body parts. In this way, the effect of motion shall be cancelled or excluded as much as possible in order to increase the accuracy and reliability of finally obtained information.

The device 12a further comprises a distance determination unit 32 for determining the physical distance between selected regions of interest. This distance can be easily determined within an image frame, e.g. by measuring the distance between the centers of the respective regions of interest. This can be done either by measuring the distance between body parts directly on a body, or by measuring the distance in pixels between coordinates of the centrums of ROIs and normalizing it to the size of the entire body in pixels.

Finally, the device 12a further comprises a calculation unit 34 for determining pulse transit time and/or pulse wave velocity information 35 from the PPG signals extracted from different regions of interest and the respective determined physical distance between the respective regions of interest.

The various units of the device 12a may be comprised in one or multiple digital or analog processors depending on how and where the invention is applied. The different units may completely or partly be implemented in software and carried out on a personal computer connected to a device for obtaining image frames of a subject, such as a camera device. Some or all of the required functionality may also be implemented in hardware, e.g. in an application specific integrated circuit (ASIC) or in a field programmable gate array (FPGA).

Arterial stiffness and Pulse Wave Velocity are generally estimated by measuring PTT, which in its turn requires synchronized measurement of PPG signals at several sites of a body. Currently, multi-site PPG measurement is performed by means of placing several contact PPG sensors on body parts (legs, arms, forehead), synchronized with each other or/and with ECG. There are several disadvantages associated with such set-up. The set-up with several synchronized PPG and ECG sensors is cumbersome, takes time to install and therefore prone to errors. The shape and arrival time of pulse at different body locations is influenced by gravitation and therefore dependent on body posture. Therefore, the exact body pose of a subject should be carefully recorded and taken into account during measurements. For sensors placed on the forehead, positioning of the sensor is crucial, since the direction of blood flow affects the pulse delays measured by the detector. Dependence of the shape of the pulse signal on placement of contact PPG sensor and the sensor construction makes accurate and reproducible measurement of PTT difficult.

In general, reproducibility of multi-site PPG measurement by means of probe attachment to a body is affected by several factors, such as probe-tissue interface pressure, motion artifacts, subject posture and relaxation, breathing, etc. Moreover, the measurement of PPG signals on limited number of body spots (e.g. only legs, hands) might be sufficient to estimate PWV, but not enough to provide other information related to monitoring of cardio vascular system. For instance, analysis of the difference of phase and shape of PPG signals between foots provides an indication of diabetes, spatial distribution of PPG amplitudes gives the information about the local condition of micro vascular blood flow and tissue viability, etc.

The proposed device and method, in contrast, can unobtrusively, reliably and synchronously measure spatial PPG information from multiple body sites simultaneously, automatically adjust to body position, respiration, body motion, and provide a set of parameters to compare shapes, phase, arrival times, amplitudes of PPG signals from multiple sites. Optionally, in an embodiment a multispectral high frame rate camera, optionally synchronized with ECG, is used for acquisition of the image data. This device can optionally contain a source of structured illumination emitted towards the chest of a subject.

In this context "spatial PPG information" means a 2D array, where each pixel represents an amplitude of extracted PPG signal. In other words, spatial PPG, breathing, or SpO2 information is generally a 2D map, where each pixel corresponds to 1D signal of PPG, breathing, or SpO2 signal extracted from either that pixel on a skin, or from an ROI around that pixel.

Figure 3:
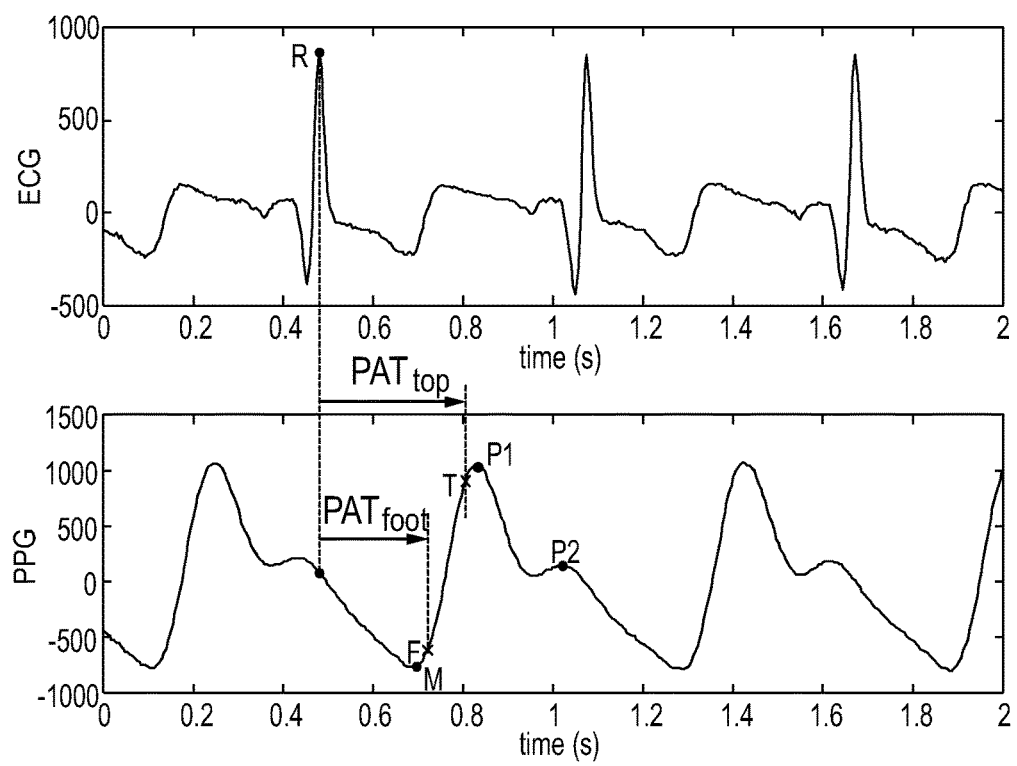
FIG. 3 shows an electrocardiogram and a photoplethysmogram for measuring a pulse arrival time according to the state of the art.

FIG. 3 shows, for illustration purposes, an electrocardiogram and a photoplethysmogram for evaluating the pulse arrival time according to the state of the art. The electrocardiogram and the photoplethysmogram are detected at different positions on the human body in order to measure the pulse transit time and to detect trends in the blood pressure from the pulse arrival time.

The pulse arrival time is usually determined as a time frame from a maximum peak R of the electrocardiogram to a certain point in time of the photoplethysmogram. The pulse arrival time may be detected as a time frame from the maximum R of the electrocardiogram to a minimum value F of the photoplethysmogram as a foot pulse arrival time $PAT_{foot}$ or to a maximum value T of the photoplethysmogram as a top pulse arrival time $PAT_{top}$ or as a time to the maximum slope of the photoplethysmogram between the maximum and the minimum value of the photoplethysmogram.

Figure 4:
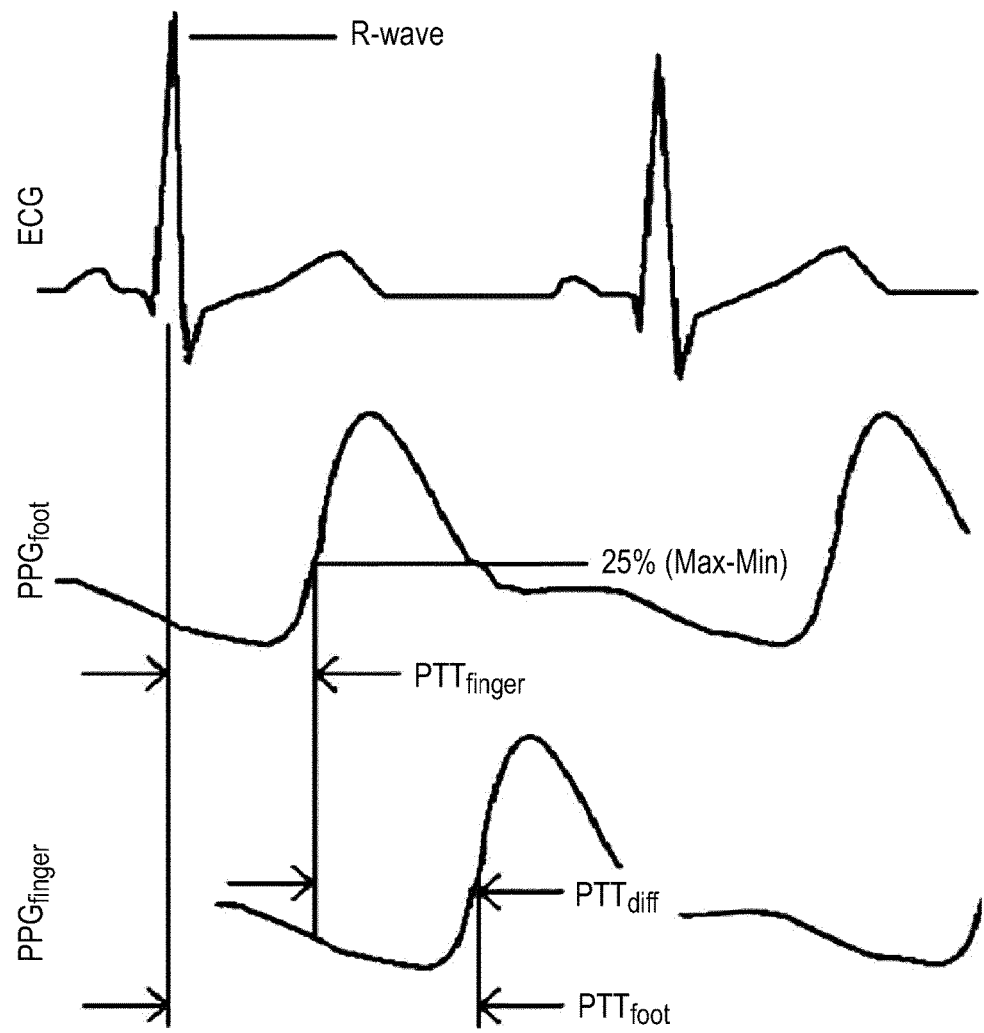
FIG. 4 shows an electrocardiogram and two PPG signals obtained at different ROIs for illustrating the determination of PTT and PWV.

FIG. 4 shows a diagram of an ECG signal and two PPG signals obtained at the hand ($PPG_{hand}$) and at the foot ($PPG_{foot}$) of a subject. Therein the pulse transit time at the hand ($PTT_{hand}$) and at the foot ($PTT_{foot}$) are indicated as well as their difference $PTT_{diff}$. The pulse wave velocity PWV is obtained by calculating $PWV=D/PTT_{diff}$, where D is the distance between the hand and the foot, i.e. the positions where the PPG signals were measured.

Figure 5:
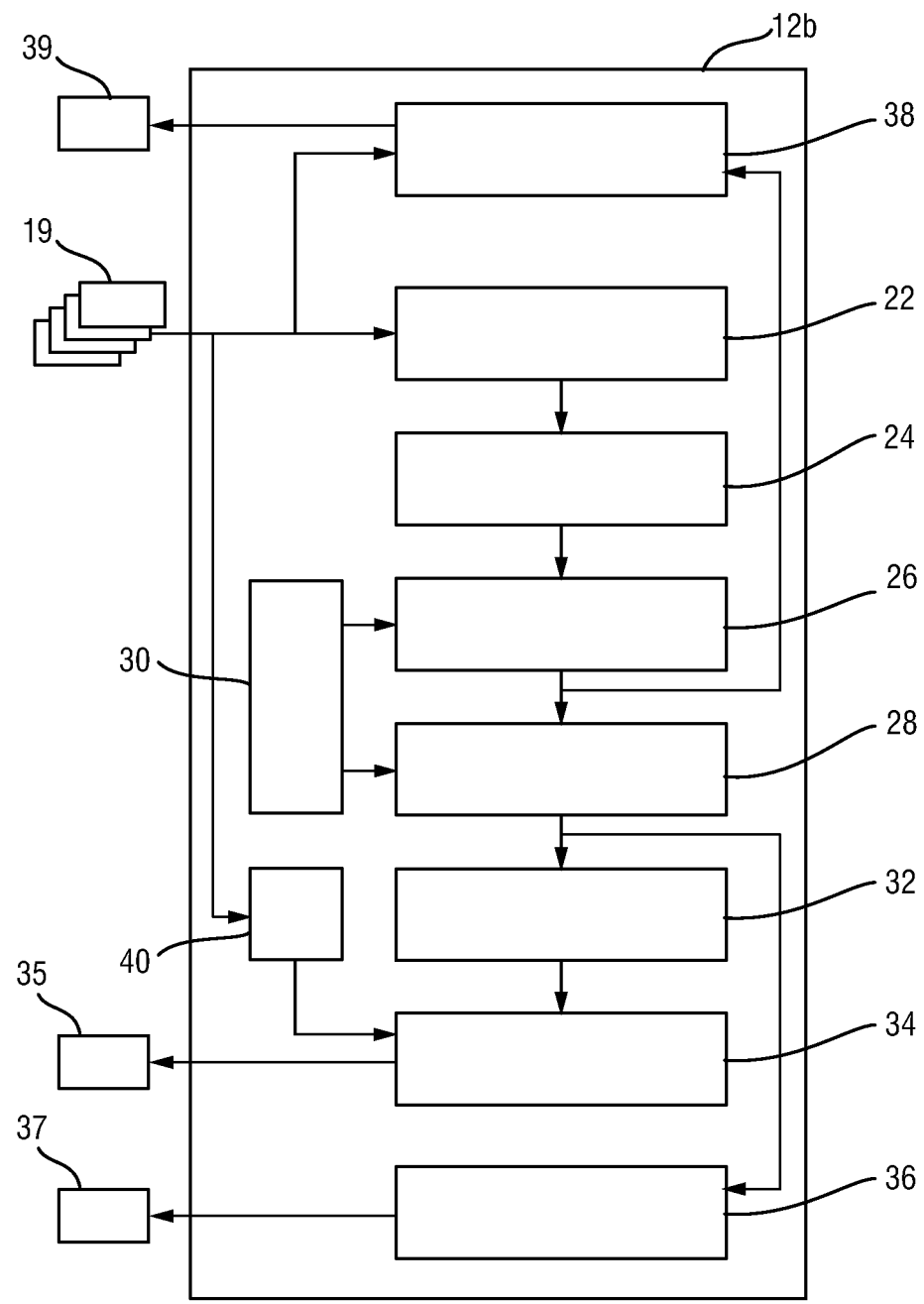
FIG. 5 shows a schematic illustration of a second embodiment of a device according to the present invention.

FIG. 5 shows another embodiment of a device 12b according to the present invention comprising some additional elements compared to the embodiment 12a shown in FIG. 2. It shall be noted however that not all of these additional elements need to be provided, in further embodiments of the device only one or more of these additional elements are provided.

In particular, the device 12b comprises a vital signs determination unit 36 for determining vital sign information 37 from the PPG signals extracted by the signal extraction unit 28 from one or more selected regions of interest. The term "vital sign" as used in the context of the present invention refers to a physiological parameter of a subject (i.e. a living being) and derivative parameters. In particular, the term "vital sign" comprises heart rate (HR) (sometimes also called pulse rate), heart rate variability (pulse rate variability), pulsatility strength, perfusion, perfusion variability, PPG pulsatility, Traube Hering Mayer waves, respiratory rate (RR), body skin temperature, blood pressure, pulse transit time (PTT), a concentration of a substance in blood and/or tissue, such as (arterial) blood oxygen saturation or glucose level. The term "vital sign information" as used in the context of the present invention comprises the one or more measured vital signs as defined above. Furthermore, it comprises data referring to a physiological parameter, corresponding waveform traces or data referring to a physiological parameter of a time that can serve for subsequent analysis.

For instance, the changes of (arterial) blood oxygen saturation at different body parts can thus be quickly determined, from which a body map indicating the determined oxygen saturation for the respective body parts can be quickly obtained. How to determine the blood oxygen saturation from PPG signals is generally known in the art and e.g. described in Wieringa, et al., "Contactless Multiple Wavelength Photoplethysmographic Imaging: A First Step Toward "SpO2 Camera" Technology," Ann. Biomed. Eng. 33, 1034-1041 (2005).

The device 12b further comprises a respiration determination unit 38 for determining respiratory information 39, in particular respiration rate and/or changes of respiration volume, of the subject 14 from said set of image frames at selected regions of interest. Respiration information is a very valuable and essential information quickly providing information about sudden changes of the subject's health condition. This respiration monitoring may e.g. be realized by detecting the subtle breathing motion in the subject's chest (or belly) area.

A usable method for determining respiratory information from image data are e.g. described in WO 2012/140531 A1 according to which electromagnetic radiation emitted and/or reflected of a person is detected, wherein this electromagnetic radiation comprises a continuous or discrete characteristic motion signal related to the respiratory rate of the person and other motion artifacts related to the movement of the person or related to ambient conditions. This method increases the reliability of the respiratory rate measurement by taking into account data processing means adapted to separate the respiratory rate signal from overall disturbances by taking into account a predefined frequency band, common predefined direction or an expected amplitude band and/or amplitude profile to distinguish the different signals.

Another usable method for inferring the respiration rate from PPG signals, which are modulated in amplitude, frequency and baseline is described in Addison et. al. J., "Developing an algorithm for pulse oximetry derived respiratory rate (RRoxi): a healthy volunteer study", Journal of Clinical Monitoring and Computation, 26:45-51 (2012). Further usable methods are also known in the art.

The device 12b further comprises a body posture detection unit 40 for detecting the body posture of the subject 14. The calculation unit 34 takes the body posture into account in the determination of the pulse transit time and/or pulse wave velocity information. The body posture, e.g. lying on the back, on the side, sitting, standing, etc., can be determined from the image data 19 by conventional image processing methods, such as pattern recognition or other algorithms. Usable methods are e.g. described in L. Panini, R. Cucchiara "A Machine learning approach for human posture detection in domotics applications", Proceedings of the 12$^{th}$ International Conference on Image analysis and Processing (ICIAP'03) and Humberto Souto Junior, Soraia Raupp Musse, "Automatic Detection of 2D Human Posture based on Single Images", Proceedings of Graphics, Patters and Images (Sibgraphi), 2011, August, 2011.

The information about the posture of the body may be used in several ways for proper calculation of PTT, PWV and evaluation of the pulse shape properties at various body locations. First of all, the posture information allows an accurate calculation of distances between ROIs on various body parts. For that, the system should know the position of a body (e.g. siting, laying, etc.) and adjust the direct distance between ROIs accordingly. Moreover, the body position influences a pulse shape of extracted PPG signals. For instance, the shape of PPG signal extracted from a palm will be very different depending whether a hand is below a heart level or above. Therefore, for proper analysis of pulse shape, the positions of body parts in relation to each other are very useful.

Preferred embodiments of the proposed device thus have one or more of the following monitoring functionalities:

Automatic estimation of body posture and/or continuous tracking of motion of body parts. This is important to correctly calculate the distances between ROIs on various body parts and to make a proper analysis of pulse shape signal.

Estimation of biometrical body parameters (length of arms, legs, distance from a palm to a heart, etc.). PPG signals extracted from different body parts would have different shape. Therefore, in order to accurately estimate the PTT/PWV and analyze (changes of) pulse shape information, estimation of biometrical body parameters are useful. However, in a basic embodiment, just a detection of body peripherals, and an analysis of PPG signals extracted from body peripherals might be sufficient.

Measurement of respiratory motion and/or estimation of respiratory rate. Breathing influences the shape of PPG signal, as well as inter peak distance of pulse signals and their amplitude. Therefore, in order to accurately analyze the differences in PPG signals extracted from various body parts, removal of the variability in PPG signals caused by respiration might be useful, as proposed in an additional embodiment of the present invention. Moreover, the breathing signal (rate, shape of respiratory signal) contains important information about the health condition of a person by itself.

Measurement of relative changes of respiratory volume (e.g. by means of analysis of structured light pattern changes during breathing). Regularity of breathing and type of breathing (belly or chest) provides an important information about the health condition of a person.

Measurement of PPG signals in different wavelengths, including at least green, red, infra-red. Monitoring of PPG signals in at least two wavelengths is required to provide robustness of PPG measurement to motion and ambient illumination, and to provide SpO2 measurements.

Analysis of PPG imaging (spatial map of PPG amplitude) of visible skin areas of a body in at least green and infra-red color channels. Changes of PPG imaging per spatial skin location can be used for evaluation of blood microcirculation, as e.g. described in U. Rubins, V. Upmalis, et al. "Real-time Photoplethysmography Imaging System", IFMBE proceedings 34, pp. 183-186, 2011. This paper describes the use of PPG imaging for monitoring of blood perfusion changes during local anesthesia. Moreover, PPG imaging can be used as a tool to automatically detect ROIs on a body with the strongest PPG signal, which will serve as reliable ROIs for PTT and PWV measurement.

Monitoring of changes of SpO2 values at different body sites. Oxygenation of arterial blood is changing over a body with different dynamics. Spatial dynamics of SpO2 changes may be used for estimation of local microcirculation in a way similar to PPG imaging.

In preferred embodiments of the device body posture and/or body motion are determined, and/or control for adaptive acquisition of vital signs is provided. In particular, based on PPG imaging skin segments are defined, which have the strongest and most reliable PPG signal (using PPG imaging, as described above), which segments are used as virtual sensors, particularly for PTT and PWV measurement. Further, an objective estimation of exact body posture is made to provide reproducibility of PTT, PWV measurements. Estimation of body motion is performed to control the acquisition of PPG signals (e.g. to stop acquisition from a particular body part, if motion of this part is detected) or to provide motion robust acquisition of PPG signals. Estimation of the respiratory motion (in particular both respiration rate and relative changes of volume), which information is used to control the acquisition and adaptive analysis of PPG signals, which would be required for accurate calculation of PTT and PWV. Further, an ECG sensor can be optionally provided for more accurate calculation and/or confirmation of PTT and PWV. In the embodiment with ECG sensor, PTT and PWV are calculated based on a time difference between peaks of ECG (reference time stamps) and peaks of pulse PPG signal from one or several body parts. In an embodiment without ECG, PTT and PWV are calculated based on time distance between beats of PPG signals acquired from different body parts.

In this context, a "virtual sensor" means an ROI on skin, wherein all pixels are preferably averaged to extract a physiological signal. For instance, if an ROI ("virtual sensor") is selected on a forehead, all pixels within this forehead ROI are averaged to extract one PPG signal. The proposed device and method can have either thousands of such ROIs/virtual sensors, or only one virtual sensor, which includes all pixels of the visible skin.

Moreover, in preferred embodiments of the device one or more of the following functionalities are provided (which are preferably carried out by the calculation unit 34 or by separate additional units):

Analyze the time difference between beats of PPG signals acquired from "virtual sensors" (i.e. the selected ROIs) located at legs, hands, and around a heart area of a person. In another embodiment of the invention, the time differences between beats of PPG signals acquired from selected ROIs are calculated with reference to beats of an ECG signal (if available)

Calculate the distance between "virtual sensors".

Calculate PTT and PWV between several pairs of "virtual sensors", taking into account the information from above two steps.

Analyze the difference in SpO2 trending between virtual sensor on a forehead and body peripherals.

Analyze the phase shift of PPG signal between two feet from "virtual sensors" located at the same distance from a heart.

Analyze the relation between respiratory volume, respiratory rate, and changes of PPG amplitude. For example, the method described in Lena Nilsson, Tomas Goscinski, et al. "Respiratory variations in the photoplethysmographic waveform: acute hypovolaemia during spontaneous breathing is not detected", 2010 Physiol. Meas. Volume 31, Number 7 or in Nilsson L, Johansson A, Kalman S., "Respiratory variations in the reflection mode photoplethysmographic signal. Relationships to peripheral venous pressure", Medical and Biological Engineering and Computing 2003 May; 41(3): 249-54 can be used for this purpose.

The imaging unit 18, which may also be part of the device 12, is preferably a video camera for acquiring PPG signals in several color channels from multiple "virtual sensors" (ROIs), from which various PPG-related information, in particular vital signs, such as SpO2, pulse shape, pulse amplitude etc. are derived. Further, respiratory rate and changes of respiratory volume can be derived from the acquired image data, e.g. by analyzing motion of a chest and/or belly area.

By analyzing the differences in PPG-related information between "virtual sensors" PTT, PWV, speed of SpO2 changes etc. can be estimated, and the dependency between respiratory efforts, respiratory volume and changes in shape, amplitude and inter-peak distances of extracted PPG signals can be analyzed.

FIG. 6 shows a flowchart of an embodiment of a method according to the present invention. In a first step S10 the image data (video data) are obtained, e.g. of the entire body of the subject, in different color channels. In step S12 visible skin areas are detected in the image data. In step S14 PPG imaging is performed for the visible skin areas. For instance, a spatial map of PPG amplitudes for some or each pixel of a skin ROI is obtained from the image data. In step S16 ROIs with the strongest PPG pulsatility are detected, which ROIs represent "virtual sensors", i.e. locations from which the signals will be used for further processing. In this step S16 information obtained from step S18, in which non-moving ROIs are detected, is additionally used, i.e. only non-moving ROIs are generally used as "virtual sensors".

In step S20 PPG signals are acquired from all detected ROIs ("virtual sensors"). In step S22 the PPG phase shift between two or more virtual sensors are analyzed. The phase shift between PPG signals acquired from various body parts will be used for calculation of PTT, PWV and eventually for arterial stiffness estimation.

In step S24 the respiratory rate, spatial breathing map and/or changes of the volume are analyzed. Based on this information and the PPG signals obtained in step S20 changes in the PPG morphology and SpO2 are analyzed in step S26 depending on the respiration.

In step S28 the distance between detected ROIs is estimated. Based on the information from steps S20 and S30 PTT, PWV and the speed of changes of SpO2 between the detected ROIs are calculated. Finally, in step S32 blood pressure changes are estimated based on the calculated PTT and PWV, for instance according to a method as disclosed in J. Sola, St. Rimoldi, and Yves Allemann, "Ambulatory monitoring of the cardiovascular system: the role of Pulse Wave Velocity", in New Developments in Biomedical Engineering, I-Tech Education and Publishing, Vienna, Austria, ISBN 978-953-7619-57-1.

According to another aspect a device is proposed for obtaining physiological information of the subject. Said device generally comprises all elements of the device 12a shown in FIG. 2, except for the distance determination unit 32. Further, the calculation unit 34 is configured differently, namely to determine physiological information of the subject including one or more of diagnosis of diabetes, evaluation of local blood microcirculation, analysis of changes of local blood perfusion by analyzing PPG signals acquired from different body parts of the subject. Multiple PPG signals extracted from different regions of interest are evaluated to perform a diagnosis of diabetes (e.g. by analyzing the difference in phase and shape of two PPG signals acquired from both feet or both legs), to monitor the local blood microcirculation and local blood perfusion acquired.

In summary, the proposed device and method allow estimating several vital signs from one video stream, analyzing the differences in morphology and temporal changes of those vital signs between several parts of a body and estimating the local vascular characteristics of different body parts at the same time. PTT and PWV are estimated from PPG signals acquired from several body sites, selected preferably based on the strength of PPG imaging and local motion information. Further, changes of blood pressure can be evaluated based on the estimated PWV.

Instead of combining various contact sensors (ECG, PPG, respiration, etc.) as conventionally done, the proposed device and method provide the same or even more functionalities. The proposed device and method thus do not just replace the functionalities of ECG, PPG, etc. sensors, but provide a functionality achieved currently only by a particular way of combination of those known sensors. For instance, currently, in order to acquire PWV, two contact PPG sensors should measure PPG signals synchronously and the analysis system must know exactly the positions of those sensors, measure the physical distance between sensors, etc. All this is replaced by the signal processing provided in the proposed device and method. By use of a (single) imaging device (e.g. camera) several vital signs of different physiological origin (PPG, breathing motion) can thus be measured from multiple locations of a body, simultaneously with context information (body motion, distance between ROIs), and signal processing can be applied to extract derivative vital signs based on combined analysis of measured physiological signals and context information.

The proposed method and device can particularly be used for quick evaluation (scan) of a cardiovascular condition of a person by measuring multiple vital signs from different parts of the body without a hassle to attach several contact sensors and provide for their synchronization. They can further be used either for a periodic scan during ambulatory cardiovascular monitoring, or for continuous monitoring to detect early deteriorations and to reliably detect severe deteriorations of the person's condition (e.g. centralization).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored or distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for obtaining pulse transit time and/or pulse wave velocity information of a subject, comprising
    an interface for receiving a set of image frames of a subject acquired by an imaging unit,
    a motion detection unit for detecting motion of body parts of the subject,
    an ROI selection unit for selecting at least two regions of interest at the body parts of the subject within said set of image frames,
    a signal extraction unit for extracting at least two photoplethysmographic (PPG) signals from at least two selected regions of interest from said set of image frames,
    a motion correction unit for controlling said ROI selection unit to select only regions of interest at substantially unmoved body parts and/or for controlling said signal extraction unit to extract one of the PPG signals only from regions of interest at substantially unmoved body parts or to correct the PPG signals extracted from regions of interest at moving body parts,
    a distance determination unit for determining within a single one of the image frames the physical distance between the selected regions of interest, and
    a calculation unit for:
        determining at least one of pulse transit time and pulse wave velocity information from the PPG signals extracted from different regions of interest and the respective determined physical distance between the respective regions of interest; and
        determining at least one body map for the body parts wherein the at least one body map indicates the determined pulse transit time and/or pulse wave velocity information and/or arterial blood oxygen saturation at the body parts derived from the PPG signals.

2. The device as claimed in claim 1,
    wherein said signal extraction unit is configured to select a plurality of regions of interest from a plurality of different body parts of the subject,
    wherein said signal extraction unit is configured to extract a plurality of PPG signals from said plurality of selected regions of interest, and
    wherein said calculation unit is configured to determine pulse transit time and/or pulse wave velocity information from the PPG signals extracted from a plurality of different regions of interest and the respective determined physical distance between the respective regions of interest.

3. The device as claimed in claim 2,
    wherein said calculation unit is configured to determine a first body map indicating the determined pulse transit time and/or pulse wave velocity information for the body parts.

4. The device as claimed in claim 1, further comprising a vital signs determination unit for determining vital sign information from the PPG signals extracted from one or more selected regions of interest.

5. The device as claimed in claim 4, wherein said vital signs determination unit is configured to determine the arterial blood oxygen saturation at the body parts and determine a second body map indicating the determined arterial blood oxygen saturation for the body parts.

6. The device as claimed in claim 1, further comprising a respiration determination unit for determining respiratory information, in particular respiration rate and/or changes of respiration volume, of the subject from said set of image frames at selected regions of interest.

7. The device as claimed in claim 1, wherein said ROI selection unit is configured to select regions of interest from which the strongest and/or most reliable PPG signals can be extracted.

8. The device as claimed in claim 1, wherein said calculation unit is configured to determine phase shifts between PPG signals extracted from different regions of interest and to determine pulse transit time and/or pulse wave velocity information from said phase shifts and the determined physical distance between the respective regions of interest.

9. The device as claimed in claim 1, further comprising:
    a body posture detection unit for detecting the body posture of the subject,
    wherein said calculation unit is configured to take the body posture into account in the determination of the pulse transit time and/or pulse wave velocity information.

10. The device as claimed in claim 1,
    wherein said calculation unit is configured to monitor said pulse transit time and/or pulse wave velocity information over time.

11. The device as claimed in claim 1,
    wherein said calculation unit is configured to determine changes in blood pressure from the determined pulse transit time and/or pulse wave velocity information and/or to determine differences in pulse shapes between PPG signals extracted from different regions of interest.

12. The device as claimed in claim 1,
    further comprising a camera for acquiring image frames of a subject.

13. A method of obtaining pulse transit time and/or pulse wave velocity information of a subject, comprising
    receiving a set of image frames of a subject acquired by an imaging unit,
    detecting motion of body parts of the subject,
    selecting at least two regions of interest at body parts of the subject within said set of image frames, extracting at least two photoplethysmographic (PPG) signals from at least two selected regions of interest from said set of image frames, controlling said ROI selection to select only regions of interest at substantially unmoved body parts and/or for controlling said signal extraction to extract a PPG signal only from regions of interest at substantially unmoved body parts or to correct PPG signals extracted from regions of interest at moving body parts, determining a physical distance between selected regions of interest within an image frame, and determining pulse transit time and/or pulse wave velocity information from the PPG signals extracted from different regions of interest and the respective determined physical distance between the respective regions of interest by determining a body map indicating the determined pulse transit time and/or pulse wave velocity information for the body parts.

14. A non-transitory computer readable medium storing instructions for causing a computer to carry out the steps of the method as claimed in claim 13 when said computer program is carried out on the computer.

15. A device for obtaining at least one of pulse transit time and pulse wave velocity information of a subject, the device comprising:
an interface configured to receive a set of image frames of a subject acquired by a camera; and
at least one processor programmed to:
detect motion of body parts of the subject;
select at least two regions of interest at the body parts of the subject within said set of image frames;
extract at least two photoplethysmographic (PPG) signals from at least two selected regions of interest from said set of image frames at substantially unmoved body parts;
determine within one of the image frames the physical distance between the selected regions of interest;
determine at least one of pulse transit time and pulse wave velocity information from the PPG signals extracted from different regions of interest and the respective determined physical distance between the respective regions of interest;
determine vital sign information from the PPG signals extracted from one or more selected regions of interest including determining an arterial blood oxygen saturation at the body parts and determining a body map indicating the determined arterial blood oxygen saturation for the body parts.

16. The device as claimed in claim 15, wherein the at least one processor is programmed to determine, from the selected regions of interest, at least one of:
arterial blood oxygen saturation;
respiration rate;
changes of respiration volume.

17. The device as claimed in claim 15, wherein the at least one processor is programmed to
select regions of interest from which the strongest and/or most reliable PPG signals can be extracted.

18. The device as claimed in claim 15, wherein the at least one processor is programmed to
determine phase shifts between PPG signals extracted from different regions of interest and to determine pulse transit time and/or pulse wave velocity information from said phase shifts and the determined physical distance between the respective regions of interest.

19. The device as claimed in claim 15, wherein the at least one processor is programmed to:
detect a body posture of the subject; and
determinate the pulse transit time and/or pulse wave velocity information from the detected body posture.

20. The device as claimed in claim 15, wherein the at least one processor is programmed to
determine changes in blood pressure from the determined pulse transit time and/or pulse wave velocity information; and
determine differences in pulse shapes between PPG signals extracted from different regions of interest.

* * * * *